United States Patent
Cifter et al.

(10) Patent No.: US 8,753,682 B2
(45) Date of Patent: *Jun. 17, 2014

(54) DUAL RELEASE ORAL TABLET COMPOSITIONS OF DEXLANSOPRAZOLE

(71) Applicant: Sanovel Ilac Sanayi Ve Ticaret Anonim Sirketi, Istanbul (TR)

(72) Inventors: Umit Cifter, Istanbul (TR); Ali Turkyilmaz, Istanbul (TR); Ibrahim Murat Uzer, Istanbul (TR); Alper Terkinli, Istanbul (TR); Levent Oner, Ankara (TR)

(73) Assignee: Sanovel Ilac Sanayi ve Ticaret Anonim Sirketi, Istanbul (TR)

( * ) Notice: Subject to any disclaimer, the term of this patent is extended or adjusted under 35 U.S.C. 154(b) by 0 days.

This patent is subject to a terminal disclaimer.

(21) Appl. No.: 14/033,956

(22) Filed: Sep. 23, 2013

(65) Prior Publication Data

US 2014/0030328 A1    Jan. 30, 2014

Related U.S. Application Data

(63) Continuation of application No. 13/101,292, filed on May 5, 2011, now Pat. No. 8,563,034.

(30) Foreign Application Priority Data

May 5, 2010 (TR) ................ 2010 03557
Jul. 28, 2010 (TR) ................ 2010 06225

(51) Int. Cl.
   *A61K 31/4439*    (2006.01)
(52) U.S. Cl.
   USPC ............... 424/465; 424/474; 424/480
(58) Field of Classification Search
   None
   See application file for complete search history.

(56) References Cited

U.S. PATENT DOCUMENTS

| 7,220,434 B2 * | 5/2007 | Desai et al. ............ 424/501 |
| 2004/0247677 A1 | 12/2004 | Oury et al. |
| 2006/0165797 A1 | 7/2006 | Plachetka |
| 2008/0076766 A1 | 3/2008 | Herold et al. |
| 2009/0098199 A1 * | 4/2009 | Lee et al. ............ 424/451 |
| 2009/0263475 A1 | 10/2009 | Manne et al. |

FOREIGN PATENT DOCUMENTS

| EP | 1 967 184 A1 | 9/2008 |
| WO | 2006/049565 A1 | 5/2006 |

OTHER PUBLICATIONS

Extended European Search Report dated Feb. 1, 2012 in European Patent Application No. 11164758.2.
Extended European Search Report dated Dec. 9, 2011 in European Patent Application No. 11164774.9.
Harianawala, A. et al., "Measurement of pH 1-10 near dissolving enteric coatings," International Journal of Pharmaceutics, vol. 247, 2002, pp. 139-146.
Metz et al., "Review Article: dual delayed release formulation of dsxlansoprazole MR, a novel approach to overcome the limitations of conventional single release proton pump inhibitor therapy," Alimentary Pharmacology & Therapeutics, Blackwell Scientific Publications Ltd., Cambridge, GB, vol. 29, No. 9, May 1, 2009, pp. 928-937.
Search Report and Written Opinion dated Mar. 1, 2011 in Turkish Patent Application No. TR201006225, filed Jul. 28, 2010.
Search Report and Written Opinion dated Mar. 2, 2011 in Turkish Patent Application No. TR201007007, filed Aug. 23, 2010.

* cited by examiner

*Primary Examiner* — David J Blanchard
*Assistant Examiner* — Daniel F Coughlin
(74) *Attorney, Agent, or Firm* — Kenyon and Kenyon LLP

(57) ABSTRACT

Dual release oral tablet compositions of dexlansoprazole or pharmaceutically acceptable salts or hydrated forms thereof and processes for the manufacture of the tablet composition and its use in the treatment of gastrointestinal disorders.

18 Claims, No Drawings

DUAL RELEASE ORAL TABLET COMPOSITIONS OF DEXLANSOPRAZOLE

CROSS REFERENCE TO RELATED APPLICATIONS

This application is based upon Turkish Patent Application No. TR201003557, filed May 5, 2010, and Turkish Patent Application No. TR201006225 filed on Jul. 28, 2010, under relevant sections of 35 USC §119, the entire contents of each application being incorporated by reference herein.

FIELD OF THE INVENTION

The present invention relates to dual release oral tablet compositions of dexlansoprazole or pharmaceutically acceptable salts or hydrated forms thereof and furthermore directed to processes for the manufacture of the tablet composition and its use in the treatment of gastrointestinal disorders.

BACKGROUND OF THE INVENTION

The active ingredient, dexlansoprazole is the R-enantiomer of lansoprazole which inhibits gastric acid secretion (a proton pump inhibitor). Its chemical name is (+)-2-[(R)-{[3-methyl-4-(2,2,2-trifluoroethoxy)pyridin-2-yl]methyl}sulfinyl]-1H-benzimidazole and its chemical structure is shown in the following Formula I.

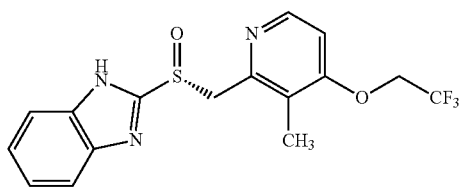

Formula I

A delayed release capsule form of dexlansoprazole is marketed and it is administered orally in a therapeutic dose of 30 mg and 60 mg.

As with other benzimidazole compounds, dexlansoprazole has also poor stability and is unstable to acidic medium, humidity, light and is sensitive to heating. When orally administered, it may not be able to sufficiently activate since it is decomposed by gastric acid and the like. Thus, several problems occur in formulating such compound into oral pharmaceutical dosage forms because of the acidic environment of the stomach. In particular, it will be rapidly decomposed and change color under moist conditions or in acidic to neutral aqueous solution.

When these compounds are formulated into pharmaceutical preparations for oral administration, they require special techniques to avoid contact of drug with gastric acid of the stomach. One technique most commonly used is to coat these compounds, or its granules or pellets, with an enteric coating. However, the material used in enteric coatings itself is acidic, which can cause decomposition of the compound. Such decomposition occurs even during the enteric coating process, which results in the coloration of the surface of the drug-containing core.

Enteric films do not show high flexibility so that compression stress can yield rupturing of the film. It is therefore necessary to use a tableting technique that endorses the compression strain and maintains the acid resistance of the formulation after compression of the granules. Therefore, caution is needed to be taken while compressing the powders and granules to form tablet dosage form. Such a formulation has to be compressed in a specific hardness.

In the prior art, there are many patents including benzimidazoles such as lansoprazole and its R-enantiomer, dexlansoprazole in several different pharmaceutical compositions. A crystal form of R-lansoprazole is described in EP-B1-1129088.

Thus, there is still a need for developing pharmaceutical formulations of dexlansoprazole wherein good stability is achieved in a technologically simple way including an improved manufacturing process which overcomes the above described problems and provides a bioavailable pharmaceutical composition according to the formulations currently used.

The pharmaceutical formulation of this invention advantageously provides a tablet dosage form which is a bioequivalent to a capsule dosage form of the same or substantially similar strength. The tablet dosage form can further be advantageous in that the manufacturing process can require fewer steps, e.g., eliminate the need for pellet formation and/or coating of those pellets, and there is no need for the additional expense of providing capsule shells.

Further advantages and embodiments of the present invention will become apparent from the following description.

SUMMARY AND DESCRIPTION OF THE INVENTION

The main object of the present invention is to provide a stable dual release oral tablet composition of dexlansoprazole or pharmaceutically acceptable salts or hydrated forms thereof previously undisclosed in the prior art which overcomes the above described problems and has additive advantages over them.

Another object of the present invention is to express a pharmacological effect of the active ingredient stably and rapidly after administration that sustains pharmacological effect of the dual release for a prolonged period of time and to have a desired release profile, wherein the release of the active ingredient, dexlansoprazole, is controlled in two steps, and the active ingredient is released in the gastrointestinal tract over a long period of time. In prior art, this dual release is obtained mostly with different enteric coatings comprising different polymers which dissolve in different pH. Because when the granules comprising the active ingredient first reach the proximal small intestine has a rapid release at pH 5.5 and the rest dissolves in distally in the small intestine at pH 6.5 to obtain the prolonged release. We obtained these two steps only with the active ingredient, dexlansoprazole having different particle size and by using hydrophobic agents described below in detail.

Yet another object of the present invention is to provide an improved and simple process for preparing the dual release oral tablet composition of dexlansoprazole or pharmaceutically acceptable salts or hydrated forms thereof.

In this invention, we had a desired dual release profile of the oral tablet compositions of dexlansoprazole or pharmaceutically acceptable salts or hydrated forms comprising dexlansoprazole in powder form in an amount of 20% and granule form in an amount of 80% wherein the granule comprises talc, colloidal silicon dioxide, magnesium stearate, hydrophobic agents, an alkali compound, fillers, binders, disintegrants or their mixtures. More specifically, the particle size ratio of dexlansoprazole powders and granules helps to provide this dual release.

As used here in, "particle size distribution" means the cumulative volume size distribution as tested by any conventionally accepted method such as the laser diffraction method. "d (0.9)" means the size at which 90% by volume of the particles are finer.

Surprisingly, this is achieved by 20% of dexlansoprazole powder having d(0.9) equal to or less than 40 μm and 80% of dexlansoprazole granule comprising talc, colloidal silicon dioxide, magnesium stearate, hydrophobic agents, an alkali compound (such as magnesium oxide), fillers, binders, disintegrants or their mixtures wherein the granules have d (0.9) equal to or less than 500 μm. In other words, the desired dual release achieved by not using pH dependent different coatings. This also prevents the dose dumping of the active ingredient, which can be a serious problem caused by the wrong design of the modified release formulations.

Dose dumping is one of the most important disadvantages of modified release dosage forms. It is difficult to develop modified release formulations for several different reasons such as having dual release profile tablet formulations, although there are many modified release formulations formulated with different coatings or using rate controlling agents. First of all, modified release formulations of these medicaments can be prone to "dose dumping" in which the release of the active ingredient is delayed but once the release begins the medicament may released rapidly. The most critical factor of dose dumping is the amount of the active substance released early on. Therefore, the active ingredient concentration in the plasma will increase suddenly and this may lead to toxicity.

According to the main object of the present invention, a dual release oral tablet composition of dexlansoprazole or pharmaceutically acceptable salts or hydrated forms is provided, said tablet comprising:
 i) 20% dexlansoprazole in powder form;
 ii) 80% dexlansoprazole granule comprising talc, colloidal silicon dioxide, magnesium stearate, hydrophobic agents, an alkali compound, fillers, binders, disintegrants or their mixtures; and
 iii) a single enteric coating that dissolves at between pH 5.5 and 6.4.

In one embodiment, the single enteric coating dissolves preferably at between pH 6.0 and 6.4.

Yet according to another object of the present invention, the particle size ratio of the dexlansoprazole in powder form to granule form has d(0.9) less than 1, and preferably less than 0.1. According to this object, the particles of the dexlansoprazole in powder form (i) has d (0.9) equal to or less than 40 μm and the particles of the dexlansoprazole granule (ii) has d (0.9) equal to or less than 500 μm.

According to another object of this present invention, to have a desired release profile and an improved stability and maximize the mechanical resistance of the tablets, this dual release oral tablet formulation has been designed to compress in a specific hardness to form the tablets wherein the compression force of the powder and granule mixture of dexlansoprazole is between 2 to 30 kN and preferably between 3 to 12 kN.

According to another object of the present invention, the hydrophobic agents of the dual release tablet in the 80% granule are selected from the group comprising hydrogenated vegetable oils such as hydrogenated castor oil; glyceryl behenate, wax, wax-like substance, fats, oils, fatty acid, fatty alcohol, shellac, pullulan, agar, gellan gum, guar gum, caragenan, acacia gum, gum arabic, dextran, pectin and their mixtures. Preferably, the hydrophobic agent is a hydrogenated vegetable oil such as hydrogenated castor oil.

In one embodiment, the enteric coating of the tablet (iii) that dissolves between at pH 5.5 and 6.4 is selected from the group comprising of cellulose acetate phthalate, cellulose acetate succinate, hydroxpropyl cellulose phthalate, hydroxpropyl ethylcellulose phthalate, hydroxyl propyl methyl cellulose phthalate, hydroxyl propyl methyl cellulose acetate succinate, hydroxyethyl cellulose phthalate, methylcellulose phthalate, polyvinyl acetate phthalate, polyvinylacetate hydrogen phthalate, amylase acetate phthalate, cellulose ester phthalates, cellulose ether phthalates, sodium cellulose acetate phthalate, starch acid phthalate, cellulose acetate butyrate, cellulose acetate maleate, cellulose acetate trimellitate, cellulose acetate propionate, styrene maleic acid dibutyl phthalate copolymer, styrene maleic acid polyvinyl acetate phthalate copolymer propionate, shellac or mixtures thereof.

In one embodiment, the amount of enteric coating layer is between 1% and 50% (w/w) of the total weight of the tablet, preferably it is 5% to 30% (w/w).

According to one embodiment, the amount of dexlansoprazole or pharmaceutically acceptable salts or hydrated forms thereof is from 5% to 50% by weight of the total tablet.

Yet another embodiment of the invention is to have a film coating under the enteric coating of the tablet so as to prevent any problems which may occur during the tablet's shelf-life. The film coating layer is selected from the group comprising of polyvinyl alcohol, polyvinylpyrrolidone (PVP), hydroxypropyl cellulose, lowsubstituted hydroxypropyl cellulose, hydroxypropylmethyl cellulose, sodium carboxymethyl cellulose, methyl and ethyl cellulose, hydroxyethyl methylcellulose, polyethylene glycol (PEG), PVP/vinyl acetate copolymer, PVA/PEG copolymer, alginates, sugar, starch, sugar alcohols (such as D-mannitol, erythritol, etc) or mixtures thereof.

The dual release oral tablet composition of this invention comprise one or more pharmaceutically acceptable excipients selected from the group comprising binders, diluents, fillers, lubricants, glidants, disintegrants, basic stabilizers, coloring agents or flavoring agents.

Suitable binders may comprise but are not limited to methyl cellulose, ethyl cellulose, hydroxypropyl methyl cellulose, hydroxypropyl cellulose, sodium carboxymethyl cellulose, polyvinyl pyrrolidone, polyvinyl alcohol, polymethacrylates, starch, gelatin, alginic acid, sucrose and the like and mixtures thereof.

Suitable diluents and fillers may comprise but are not limited to microcrystalline cellulose, cellulose, lactose, starch, calcium phosphates, calcium sulphates, mannitol, glucose, sucrose, sorbitol and the like and mixtures thereof.

Suitable lubricants may comprise but are not limited to stearic acid, magnesium, calcium or sodium stearate, sodium stearyl fumarate, talc, waxes, liquid paraffin, and the like and mixtures thereof.

Suitable glidants may comprise but are not limited to talc, aluminium silicate, colloidal silica, starch and the like and mixtures thereof.

Suitable disintegrants may comprise but are not limited to alginic acid and salts, sodium carboxymethyl cellulose, hydroxypropyl methyl cellulose, starch, sodium starch glycolate, crosslinked polyvinyl pyrrolidone and the like and mixtures thereof.

The dual release oral tablet compositions of this invention are administrated once-a-day or twice-a-day.

In one embodiment, the dual release oral tablet compositions of dexlansoprazole or pharmaceutically acceptable salts or hydrated forms thereof of this invention is obtained by the in vitro dissolution profiles tested.

In this present invention, surprisingly the problem is also solved by a more efficient process to prepare a dual release oral tablet composition of dexlansoprazole or pharmaceutically acceptable salts or hydrated forms thereof, comprising the following steps:

a) dexlansoprazole is blended in a powder blender till the adequate particle size is obtained, and then divided into the ratios described below;

b) 80% dexlansoprazole is dry mixed with one or more pharmaceutically acceptable excipient in a powder blender;

c) blended powder is then granulated by slug compression or a roller compactor and sieved to obtained granules of size <500 μm;

d) these granules are then blended with the rest of (20%) dexlansoprazole powder and any one or more pharmaceutically acceptable excipients;

e) the granules are compressed into tablets; and f) the tablets are coated with an enteric coating that dissolves between at pH 5.5 and 6.4.

The dual release oral tablet composition of dexlansoprazole or pharmaceutically acceptable salts or hydrated forms thereof is used for the treatment of gastrointestinal disorders.

As apparent from the example below, by the method of the present invention the hardness of the tablet is improved. In addition, dissolution and stability is also improved.

This invention is further defined by reference to the following example. Although the example is not intended to limit the scope of the present invention, it should be considered in the light of the description detailed above. It will be apparent to those skilled in the art that many modifications, both to materials and methods, may be practiced without departing from the scope of the invention.

EXAMPLE 1

Dexlansoprazole is blended in a powder blender until it has d(0.9) equal to or less than 40 μm is obtained, and then divided into the ratios described below. 80% of dexlansoprazole and suitable excipients are blended together in a dry powder blender for about 20 minutes. The powder is then compressed into slugs using suitable compression equipment and compression strength. These granules are then sieved to obtain a maximum granule size of <500 μm. These granules are then blended with the rest of dexlansoprazole (20%) powder and other excipients, such as magnesium stearate. The final blend is then compressed into tablets with a rotary tablet press using a compression strength of about 5 to 10 kN. These tablets are then coated in a pan coater with the aforementioned enteric coating and optionally with a film coating coating up to an approximate weight gain of about 10%.

The invention claimed is:

1. A dual release oral tablet of dexlansoprazole or pharmaceutically acceptable salts or hydrated forms thereof, said tablet comprising:

a) 20% by weight of the dexlansoprazole in powder form;

b) 80% by weight of the dexlansoprazole in granule form, said granule further comprising talc, colloidal silicon dioxide, magnesium stearate, hydrophobic agents, an alkali compound, fillers, binders, disintegrants or their mixtures, wherein the granule form is of different particle size than the powder form; and c) a single enteric coating that dissolves at between pH 5.5 and 6.4, wherein, upon oral administration, the tablet achieves dual release of the dexlansoprazole in the small intestine at pH 5.5 and then at pH 6.5, with prevention of dose dumping of the dexlansoprazole.

2. The dual release oral tablet according to claim 1, wherein the particle size ratio of the dexlansoprazole in powder form to granule form has d(0.9) less than 1.

3. The dual release oral tablet according to claim 1, wherein the particle size ratio of dexlansoprazole in powder from to granule form has d(0.9) less than 0.1.

4. The dual release oral tablet according to claim 1, wherein the particles of the dexlansoprazole in powder form (i) has d(0.9) equal to or less than 40 μm.

5. The dual release oral tablet according to claim 1, wherein the particles of the dexlansoprazole granule (ii) has d(0.9) equal to or less than 500 μm.

6. The dual release oral tablet according to claim 1, wherein the compression force to form the tablet is between 2 to 30 kN.

7. The dual release oral tablet according to claim 1, wherein the compression force to form the tablet is between 3 and 12 kN.

8. The dual release oral tablet according to claim 1, wherein the hydrophobic agents are selected from the group comprising hydrogenated vegetable oils such as hydrogenated castor oil; glyceryl behenate, wax, wax-like substance, fats, oils, fatty acid, fatty alcohol, shellac, pullulan, agar, gellan gum, guar gum, carageenan, acacia gum, gum arabic, dextran, pectin and their mixtures.

9. The dual release oral tablet according to claim 1, wherein the enteric coating that dissolves at between pH 5.5 and 6.4 is selected from the group comprising of cellulose acetate phthalate, cellulose acetate succinate, hydroxpropyl cellulose phthalate, hydroxpropyl ethylcellulose phthalate, hydroxyl propyl methyl cellulose phthalate, hydroxyl propyl methyl cellulose acetate succinate, hydroxyethyl cellulose phthalate, methylcellulose phthalate, polyvinyl acetate phthalate, polyvinylacetate hydrogen phthalate, amylase acetate phthalate, cellulose ester phthalates, cellulose ether phthalates, sodium cellulose acetate phthalate, starch acid phthalate, cellulose acetate butyrate, cellulose acetate maleate, cellulose acetate trimellitate, cellulose acetate propionate, styrene maleic acid dibutyl phthalate copolymer, styrene maleic acid polyvinyl acetate phthalate copolymer propionate, shellac or mixtures thereof.

10. The dual release oral tablet according to claim 1, wherein the amount of enteric coating layer is between 1% and 50% (w/w) of the total weight of the tablet.

11. The dual release oral tablet according to claim 9, wherein the amount of enteric coating layer is between 1% and 50% (w/w) of the total weight of the tablet.

12. The dual release oral tablet according to claim 1, wherein the amount of enteric coating layer is between 5% and 30% (w/w) of the total weight of the tablet.

13. The dual release tablet according to claim 9, wherein the amount of enteric coating layer is between 5% and 30% (w/w) of the total weight of the tablet.

14. The dual release oral tablet according to claim 1, further comprising a film coating under the enteric coating.

15. The dual release oral tablet according to claim 14, wherein the film coating is selected from the group comprising of polyvinyl alcohol, polyvinylpyrrolidone (PVP), hydroxypropyl cellulose, lowsubstituted hydroxypropyl cellulose, hydroxypropylmethyl cellulose, sodium carboxymethyl cellulose, methyl and ethyl cellulose, hydroxyethyl methylcellulose, polyethylene glycol (PEG), PVP/vinyl acetate copolymer, PVA/PEG copolymer, alginates, sugar, starch, sugar alcohols (such as D-mannitol, erythritol, etc) or mixtures thereof.

16. The dual release oral tablet according to claim 1, wherein one or more pharmaceutically acceptable excipients are selected from the group comprising binders, diluents, fillers, lubricants, glidants, stabilizing agents, coloring agents, flavouring agents and the like and mixtures thereof.

17. A process for preparing a dual release oral tablet of dexlansoprazole or pharmaceutically acceptable salts or hydrated forms thereof, said process comprising the following steps:
 a) blending dexlansoprazole in a powder blender until the adequate particle size is obtained, and then divided into the ratios described below;
 b) dry mixing 80% dexlansoprazole with one or more pharmaceutically acceptable excipient in a powder blender;
 c) granulating the blended powder by slug compression or a roller compactor and sieving to obtain granules of size <500 μm;
 d) blending these granules with the rest of (20%) dexlansoprazole powder and any one or more pharmaceutically acceptable excipients;
 e) compressing the granules into tablets; and
 f) coating the tablets with an enteric coating that dissolves between at pH 5.5 and 6.4.

18. The dual release oral tablet of dexlansoprazole or pharmaceutically acceptable salts or hydrated forms thereof according to claim 1, for use in the treatment of gastrointestinal disorders.

* * * * *